United States Patent [19]
Shaw

[11] Patent Number: 6,051,739
[45] Date of Patent: Apr. 18, 2000

[54] PROCESS FOR PRODUCING ORGANIC POLYSULFIDES

[75] Inventor: James E. Shaw, Bartlesville, Okla.

[73] Assignee: Phillips Petroleum Company, Bartlesville, Okla.

[21] Appl. No.: 09/236,976

[22] Filed: Jan. 26, 1999

[51] Int. Cl.$^7$ .................. C07C 321/12; C07C 319/22
[52] U.S. Cl. .............................................. 568/26; 568/21
[58] Field of Search .................................... 568/21, 25, 26

[56] References Cited

U.S. PATENT DOCUMENTS

| | | | |
|---|---|---|---|
| 5,218,147 | 6/1993 | Shaw | 568/21 |
| 5,232,623 | 8/1993 | Shaw | 252/183.13 |
| 5,530,163 | 6/1996 | Shaw | 568/26 |
| 5,861,539 | 1/1999 | Shaw | 568/26 |
| 5,907,064 | 5/1999 | Shaw | 568/21 |

*Primary Examiner*—Gary Geist
*Assistant Examiner*—Jean F Vollano
*Attorney, Agent, or Firm*—Richmond, Hitchcock, Fish & Dollar

[57] ABSTRACT

A process for producing an organic polysulfide compound comprises contacting, in the presence of a catalyst, a mercaptan with elemental sulfur to produce a product medium and contacting the product medium with a material comprising carbon dioxide or a carbon dioxide-generating compound wherein the catalyst comprises a base and optionally a surfactant and the organic polysulfide contains about 3 or more sulfur atoms per molecule.

20 Claims, No Drawings

PROCESS FOR PRODUCING ORGANIC POLYSULFIDES

The present invention relates to a process for producing an organic polysulfide compound.

BACKGROUND OF THE INVENTION

Organic polysulfides such as alkyltrisulfides are useful for many purposes such as additive for elastomers, as antioxidants for lubricating oils, as intermediate for the production of organic chemicals, insecticides, and germicides and as additive to diesel fuels to improve the cetane number and ignition qualities of these fuels. These compounds are also useful in the compounding of extreme pressure lubricants and in the acceleration of rubber treating processes.

Such polysulfide compounds can be produced by reacting mercaptans with elemental sulfur in the presence of a basic catalyst. For example, Shaw (U.S. Pat. No. 5,530,163) discloses that organic polysulfides can be produced from a mercaptan and sulfur catalyzed by a basic catalyst.

A conventional process for producing an organic polysulfide is to react a mercaptan with elemental sulfur. However, the polysulfide thus produced is generally associated with some unreacted mercaptans and dissolved $H_2S$, both of which contribute to unpleasant odor. Additionally, possibly because of the unreacted mercaptan and/or the catalyst, the polysulfide thus produced generally becomes unstable, i.e., the polysulfide turns cloudy, upon storage. The mercaptan content can also increase with storage. The instability and odor greatly reduce the desirability and utility of organic polysulfides.

Therefore, there is an increasing need to develop a process for producing a substantially odor-reduced and substantially a stable organic polysulfide.

SUMMARY OF THE INVENTION

An object of the present invention is to provide a process for producing an organic polysulfide. An advantage of the present invention is the organic polysulfide is stable during the workup or storage. Other objects and advantages will become more apparent as the invention is more fully disclosed hereinbelow.

According to the present invention, a process for producing an organic polysulfide is provided which comprises, consists essentially of, or consists of contacting a mercaptan with elemental sulfur in the presence of a catalyst wherein the catalyst comprises a base and optionally a surfactant to produce a product medium comprising the polysulfide and thereafter the product medium is contacted with a polysulfide-stabilizing material which comprises carbon dioxide or a carbon dioxide-generating compound.

DETAILED DESCRIPTION OF THE INVENTION

According to the present invention, the term "stable" refers to a polysulfide compound that does not substantially turn cloudy or hazy or increase mercaptan content, during the production or storage for at least about 30 days, preferably about 6 months. The term "substantial" or "substantially" means more than trivial.

According to the present invention, an organic polysulfide compounds having the formula of $R$—$S_q$—$R$, wherein each R can be the same or different and are each a hydrocarbyl radical having 1 to about 30, preferably about 1 to about 20, and most preferably 2 to 15 carbon atoms and q is a number from 2 to about 10, preferably 2 to 8, more preferably 3 to 5, and most preferably 3, can be produced by a process of the present invention. The hydrocarbyl radical can be linear or branched and can be alkyl, aryl, cycloalkyl, alkaryl, aralkyl, alkenyl radicals, or combinations of any two or more thereof. Preferably the hydrocarbyl radical is an alkyl radical. The presently most preferred organic sulfide compounds are di-t-butyl trisulfide and di-t-dodecyl trisulfide.

The term "stable organic polysulfide" or "stable organic polysulfide compound" used in the present application, unless otherwise indicated, denotes an organic polysulfide compound which does not substantially or significantly change the number of sulfur atoms per molecule of the organic polysulfide, or which has reduced susceptibility to decomposition, when the organic polysulfide is further processed by a physical treatment or is stored. The physical treatment can include purification, separation, recovery, or combination of two or more thereof. Examples of such physical treatments include, but are not limited to, distillation, gas sparging, mixing, heating, chromatographic separation, recovery, or combination of two or more thereof. For example, a stable organic trisulfide is an organic polysulfide is an organic polysulfide compound, when it is processed such as, for example, distilled under reduced pressure, is not substantially or significantly decomposed to an organic disulfide or does not substantially or significantly increase the sulfur atoms in the trisulfide to, for example, tetrasulfide or pentasulfide.

According to the present invention, the base useful as a component of the catalyst can be an organic or an inorganic base, or combinations of two or more thereof. Suitable organic bases include, but are not limited to, trimethylamine, triethylamine, methylamine, ethylamine, dimethylamine, diethylamine, other amines, tetramethylammonium hydroxide, tetraethylammonium hydroxide, tetrapropylammonium hydroxide, tetramethylammonium bisulfide, tetraethylammonium bisulfide, and combinations of two or more thereof. Suitable inorganic bases include, but are not limited to, lithium hydroxide, sodium hydroxide, sodium hydrogensulfide, sodium sulfide, potassium hydroxide, potassium hydrogensulfide, calcium hydroxide, magnesium hydroxide, sodium bicarbonate, sodium carbonate, sodium oxide, magnesium oxide, calcium oxide, calcium carbonate, sodium phenoxide, barium phenoxide, calcium phenoxide, $R^1ONa$, $R^1SNa$, and combinations of two or more thereof; where $R^1$ is a $C_1$–$C_{18}$ alkyl radical. Presently, an inorganic base is preferred. Among the inorganic bases, sodium hydroxide is preferred because it is readily available and inexpensive.

According to the present invention, an aqueous medium denotes, unless otherwise indicated, a reaction medium, which does not contain substantial concentration of an organic solvent. Generally, an aqueous medium can comprise regular tap water, deionized water, distilled water, a solution, a suspension, and combinations of two or more thereof. Presently it is preferred that regular tap water be used because it is readily available and economical. According to the present invention, any surfactant that facilitates the mixing of reactants into substantially a single phase can be used. The term "substantial" or "substantially" means more than trivial. The term "fluid" denotes liquid, gas, or combinations thereof.

Generally, the surfactant comprises one or more compounds which exhibit surface-active properties. A preferred surfactant for use in the reaction system of the present invention is selected from the group consisting of alkoxylated compounds, quaternary ammonium salts, alkali metal alkyl sulfates, alkali metal salts of alkanoic acids, alkali metal salts of alkaryl sulfonic acids, 1-alkyl pyridinium salts, and combinations of two or more thereof.

The presently preferred surfactant is an alkoxylated compound. Examples of suitable alkoxylated compounds include, but are not limited to, alkoxylated alcohols, alkoxylated mercaptans, sulfates of alkoxylated alcohols, alkoxylated phenols, sulfates of alkoxylated phenols, and combinations of two or more thereof.

The alkoxylated alcohol useful in the present invention has a general formula of $R^2O[CH_2CH(R^3)O]nH$ where $R^2$ is a $C_1$–$C_{20}$ hydrocarbyl radical selected from the group consisting of alkyl radical, alkylaryl radical, aryl radical, cycloalkyl radical, alkenyl radical, and combinations of two or more thereof. Preferably $R^2$ is a $C_6$–$C_{18}$ alkyl radical. Most preferably $R^2$ is a $C_{10}$–$C_{16}$ alkyl radical; $R^3$ is selected from the group consisting of hydrogen, $C_2$–$C_6$ alkyl radicals, $C_2$–$C_{16}$ alkenyl radicals, and combinations of two or more thereof; and n is a number of from 1 to about 20, preferably from about 2 to about 12, most preferably from 5 to 10. Generally $R^3$ can contain from 0 to about 16 carbon atoms. Preferably $R^3$ is a hydrogen or a $C_1$–$C_3$ alkyl radical. Most preferably $R^3$ is hydrogen. An example of suitable alkoxylated alcohol is TERGITOL® 15-S-7 which is an ethoxylated alcohol, is manufactured and marketed by Union Carbide Corporation, and has the formula of $R^2O(CH_2CH_2O)_7H$ where $R^2$ is a secondary alkyl radical having 11–15 carbon atoms and 7 is the averaged number of the ethylene oxide units. Another example is an ethoxylated phenol having the same number of ethylene oxide units. Other suitable alkoxylated alcohols are also available from Union Carbide Corporation.

The sulfate of alkoxylated alcohol useful in the present invention has a general formula of $R^2O[CH_2CH(R^3)O]_nSO_3M$ where $R^2$, $R^3$, and n are the same as those described above and M is an alkali metal or an alkaline earth metal or combinations of two or more thereof. An example of suitable sulfate of alkoxylated alcohol is sodium sulfate of an ethoxylated alcohol having the formula of $R^2O(CH_2CH_2O)_nSO_3Na$ in which $R^2$ and n are the same as those disclosed above.

Useful alkoxylated phenols and sulfates of alkoxylated phenols can have general formulas of $(R^3)_pArO[CH_2CH(R^3)O]_nH$ and $(R^2)_pArO[CH_2CH(R^3)O]_nSO_3M$, respectively where $R^2$, $R^3$, n and M are the same as those disclosed above, Ar is an aryl group, preferably a phenyl group, and p is an integer ranging from 0 to 5. Examples of these alkoxylated phenols are ethoxylated phenol $ArO(CH_2CH_2O)_nH$ and sodium sulfate of ethoxylated phenol $ArO(CH_2CH_2O)_nSO_3Na$ where Ar and n are the same as disclosed above.

The alkoxylated mercaptan useful in the present invention has a general formula of $R^2S[CH_2CH(R^3)O]_nH$ where $R^2$, $R^3$, and n are the same as those described above. An example of an alkoxylated mercaptan is an ethoxylated mercaptan having the formula of $R^2S(CH_2CH_2O)_7H$ where $R^2$ is primarily a tertiary dodecyl group and 7 is the averaged number of ethylene oxide units. This ethoxylated mercaptan is a surfactant, available under the trade name AQUA-CLEEN® II. Another example is an ethoxylated thiophenol having the same number of ethylene oxide units. Other suitable alkoxylated mercaptans are also available from Phillips Petroleum Company.

Quaternary ammonium salt useful in the present invention has the general formula $(R^4)_4N^+X^-$ where $R^4$ is an alkyl radical of from 1 to 20 carbon atoms; and X is selected from the group consisting of $Br^-$, $Cl^-$, $I^-$, $F^-$, $R^4CO_2^-$, $QSO_3^-$, $BF_4^-$, and $HSO_4^-$, where Q is an aryl, alkaryl or arylalkyl radical of 6 to 10 carbon atoms. It will be noted that a variety of anions are suitable as the component of the quaternary ammonium salts.

Useful quaternary ammonium salts according to the general formula given above include, but are not limited to, methyltrialkyl($C_8$–$C_{10}$)ammonium chloride (also known as Adogen® 464), cetyltrimethylammonium bromide, hexadecyltrimethylammonium bromide, tetraheptylammonium bromide, cetyltrimethylammonium stearate, benzyltributylammonium chloride, benzyltriethylammonium bromide, benzyltrimethylammonium bromide, phenyltrimethylammonium bromide, phenyltrimethylammonium iodide, tetrabutylammonium bromide, tetrabutylammonium chloride, tetrabutylammonium hydrogen sulfate, tetrabutylammonium iodide, tetraethylammonium bromide, tetrabutyl ammonium fluoride, tetrabutylammonium tetrafluoroborate, and combinations of two or more thereof.

An alkali metal alkyl sulfate of the general formula of $R^4OSO_3M$ can be used in the present invention, wherein $R^4$ and M are the same as those disclosed above. Examples of suitable compounds according to the general formula for the alkali metal alkyl sulfates include, but are not limited to, lithium decylsulfate, potassium dodecylsulfate, sodium dodecylsulfate, sodium hexadecylsulfate, potassium hexadecylsulfate, rubidium dodecylsulfate, cesium dodecylsulfate, sodium octadecylsulfate, potassium octadecylsulfate, potassium eicosylsulfate, sodium eicosylsulfate, and combinations of two or more thereof.

Useful alkali metal salts of alkanoic acids have the general formula of $R^4CO_2M$, where $R^4$ and M have the same meaning as given above. Examples of suitable alkali metal salts of alkanoic acids include, but are not limited to, lithium decanoate, sodium dodecanoate, potassium dodecanoate, rubidium dodecanoate, cesium dodecanoate, sodium hexadecanoate, potassium hexadecanoate, sodium octadecanoate, potassium octadecanoate, sodium eicosanoate, potassium eicosanoate, and combinations of two or more thereof.

Useful alkali metal salts of alkaryl sulfonic acids have the general formula of $(R^4)_pArSO_3M$ where $R^4$ and M are the same as those disclosed above, Ar is an aryl group or a phenyl group, and p is an integer ranging from 0 to 5. Typical compounds within the group include, but are not limited to, sodium dodecylbenzenesulfonate, potassium dodecylbenzenesulfonate, lithium dodecylbenzenesulfonte, sodium tetradecylbenzenesulfonate, potassium hexadecylbenzenesulfonate, rubidium dodecylbenzenesulfonate, cesium dodecylbenzenesulfonate, sodium octadecylbenzenesulfonte, potassium octadecylbenzenesulfonate, sodium eicosylbenzenesulfonate, and combinations of two or more thereof.

Examples of suitable 1-alkyl pyridinium salts include, but are not limited to, 1-dodecylpyridinium para-toluenesulfonate, 1-dodecylpyridinium chloride, 1-hexadecylpyridinium chloride, 1-hexadecylpyridinium para-toluenesulfonate, 1-decylpyridinium chloride, 1-hexadecylpyridinium bromide, 1-tetradecylpyridinium chloride, 1-octadecylpyridinium chloride, 1-eicosylpyridinium chloride, 1-octadecylpyridinium benzenesulfonate, and combinations of two or more thereof.

The weight ratio of surfactant to base can vary widely, preferably in the range of from about 0.001:1 to about 1000:1, more preferably about 0.01:1 to about 100:1, and most preferably from about 0.1:1 to 50:1 for best results. If a combination of bases is used, the weight ratio of one base to the other base can be in the range of from about 0.01:1 to about 100:1.

The catalyst can be made by properly mixing the base and surfactant, if used, in the ratio described above employing any suitable mixing means such as shaking or stirring. Presently, it is preferred that the catalyst be produced in-situ by adding a base and a surfactant to a reaction vessel or reactor that is used for producing an organic polysulfide.

The organic polysulfide can be produced by the reaction of mercaptans and elemental sulfur catalyzed by the catalyst disclosed above. The reaction is depicted as $RSH+RSH+(q-1)S \rightarrow RS_qR+H_2S$ where R and q are the same as those described above. The reaction can be carried out in any suitable reaction vessel. The choice of reaction vessel is a matter of preference to those skilled in the art.

The suitable conditions for the contacting of mercaptan with sulfur can include a temperature in the range of from about 20° C. to about 250° C., preferably from 50° C. to 150° C. and a time of from about 10 minutes to about 10 hours, preferably 30 minutes to 5 hours. The pressure can vary widely from about 1 atmosphere to about 30 atmospheres, preferably from about 1 atmosphere to about 10 atmospheres.

Generally, one of the reactants, either the mercaptan or sulfur, is added to the other reactant in the presence of the catalyst described above to form a reaction mixture. The molar amount of sulfur added depends on the desired sulfur content of the polysulfide and generally are shown in the above equation. For example, for an average sulfur content of q per molecule of polysulfide, (q-1) moles of sulfur are reacted with 2 moles of mercaptan. The weight of the catalyst (base and surfactant, if used) as a percentage of the weight of mercaptan is generally in the range of from 0.01 to 50%, preferably about 0.05 to 20%, and most preferably 0.1 to 10%.

During the reaction, residual hydrogen sulfide produced is generally removed or allowed to escape from product mixture or reaction vessel which contains the crude organic polysulfide product, for example, continuously or periodically venting off $H_2S$. Any unreacted mercaptan is generally removed by any means known to one skilled in the art such as, for example, distillation.

The product mixture, whether it has been further processed or not, is then contacted with a polysulfide-stabilizing material which comprises carbon dioxide or a carbon dioxide-generating compound. The material can be a gas, liquid, solid, or combinations of two or more thereof and can contain about 0.1 to about 100 weight % of carbon dioxide or carbon dioxide-generating compound. For example, air contains carbon dioxide and can be used. The presently preferred is carbon dioxide for it is readily available.

The amount of carbon dioxide required is the amount that can produce a polysulfide that is substantially stable during production workup and during storage of the polysulfide. Generally, the amount can be in the range of from about 0.1 to about 100,000, preferably about 0.5 to about 10,000, and most preferably 1 to 1,000 molar equivalent of the base used in the catalyst. The amount of carbon dioxide-generating compound is the amount that can generate the amount of carbon dioxide disclosed above.

Any carbon dioxide-generating compound can be used to purify the organic polysulfide product. Examples of suitable carbon dioxide-generating compounds such as ammonium bicarbonate, sodium bicarbonate, and combinations thereof can be used.

The contacting of the reaction medium with the fluid containing carbon dioxide or carbon dioxide-generating compound can be carried out under any conditions that are effective to produce a stable polysulfide or that can reduce the susceptibility of the organic polysulfide to decomposition during heating, during distillation of unreacted mercaptan, or sparging, of the reaction medium. Such conditions can be the same conditions employed for contacting mercaptans with elemental sulfur, as disclosed above.

The contacting of the reaction medium with the material can be carried out before the removal of the residual hydrogen sulfide or immediately after the removal of the residual hydrogen sulfide. However, such contacting is carried out before, during, or after the reaction medium is heated. For example, the reaction medium is contacted with the material before the reaction is distilled to remove unreacted mercaptan and later sparging with nitrogen. Residual hydrogen sulfide formed is generally removed from the crude organic polysulfide product by either an inert gas, such as nitrogen, purge or by vacuum stripping. Thereafter, if necessary, the organic polysulfide product can be further stabilized using any known methods such as, for example, those disclosed in the U.S. Pat. Nos. 5,206,439; 5,218,147; and 5,530,163, disclosures of which are incorporated herein by reference. For example, the polysulfide-containing product medium can also be contacted with alkylene oxide such as propylene oxide, disclosed in U.S. Pat. No. 5,218,147, and a base in a solvent such as methanol before the contacting with the polysulfide-stabilizing material disclosed in this invention.

The stable organic polysulfide compound thus produced can be further processed such as purification, separation, recovery, or combinations of any two or more thereof by any methods known to one skilled in the art such as, for example, distillation. Thereafter, if necessary, the organic polysulfide product can be further stabilized using any known methods such as, for example, those disclosed in the U.S. Pat. Nos. 5,206,439; 5,218,147; and 5,530,163, disclosures of which are incorporated herein by reference.

The process of the invention can also be carried out continuously. For example, the contacting of mercaptans with organic polysulfide in the presence of the catalyst can be done by employing continuous stir tank reactors connected in series, packed columns or towers in which the invention catalyst is supported on a solid support, and other continuous flows that are readily within the realm of one skilled in the art.

The following examples are provided to further illustrate the practice of the invention and are not intended to limit the scope of the invention of the claims.

EXAMPLE I

This example illustrates the production of di-t-butyl polysulfide.

To a 250 ml, 3-necked flask equipped with a thermowell, magnetic stirring bar, pressure equalizing addition funnel, and condenser with outlet tube on top connected to the flare line was added 0.170 g of aqueous 25% NaOH solution, 0.48 g of TERGITOL® 15-S-7 (Union Carbide), and 16.87 g of elemental sulfur. To the addition funnel was added 76.1 g of t-butyl mercaptan. The mercaptan was added in portions to the reaction flask and when enough liquid was in the flask, it was stirred and heated to 50° C. Alternatively, the sulfur can be added in portions to the mercaptan. Hydrogen sulfide was evolved during the addition. After all the mercaptan was added, the reaction mixture was heated at 60° C. for one hour with stirring. GC analysis (20 inch×⅛ inch 2% OV-101 packed column, 50° C. initially, then ramping at 15° C./minute till 200° C., injection port at 150° C. to avoid decomposition, FID detector) at this point showed that the reaction product excluding the excess mercaptan consisted of 92% di-t-butyl trisulfide, 5% di-t-butyl tetrasulfide, and 2% disulfides.

After cooling to near room temperature (25° C.), pure gaseous $CO_2$ was bubbled into the reaction mixture at 1–2 SCFH (standard cubic feet per hour) for 0.5 hours. The addition funnel and condenser were removed, and the reaction flask was connected to a vacuum pump for vacuum distillation to remove unreacted t-butyl mercaptan. The pressure was reduced to 400 torr and the reaction mixture was heated to 130° C. and maintained at 130° C. for 1.5 hours at 400 torr. Unreacted t-butyl mercaptan was collected in a trap for recycling. Then the pressure was raised back to atmospheric, and the reaction mixture was sparged with $N_2$ at 130° C. for 2 hours to remove the small amount of t-butyl mercaptan which was not removed in the vacuum distillation. After cooling, the reaction mixture was filtered to give 55.1 g of a clear yellow liquid. The yield of trisulfide was 99.5% based on elemental sulfur. GC analysis showed that the liquid consisted of 92% di-t-butyl trisulfide, 5% tetrasulfide, and 2% disulfides. Comparison of these GC results with those above show that after addition of $CO_2$ and vacuum distillation and sparging, there was no change in the product. The product was stable during the workup due to the $CO_2$ treatment.

EXAMPLE II

This example also illustrates the production of di-t-butyl polysulfide.

This run was the same as above except that instead of bubbling in $CO_2$, small amounts of dry ice were added to the reaction mixture with stirring over 0.5 hours, so that it was always bubbling with $CO_2$ gas. The results were the same as above.

EXAMPLE III

This example is a comparative example illustrating an organic polysulfide was produced without the use of carbon dioxide.

The run was carried out the same way as described in Example I except that 0.15 g of 50% aqueous NaOH, 1.06 g of TERGITOL® 15-S-7, 135.3 g of t-butyl mercaptan, and 33.0 g of sulfur were used. Carbon dioxide was not added before vacuum distillation. The vacuum distillation was carried out at 60° C. and 25 torr. GC analysis was performed each hour. The GC analyses are shown in the following Table I.

TABLE I

| Hours of vacuum distillation | Weight % by GC | | | | |
|---|---|---|---|---|---|
| | Disulfide | Trisulfide | Tetra-sulfide | Penta-sulfide | Mercaptan |
| 0 | 1.6 | 61.0 | 6.1 | 0.1 | 30.8 |
| 1 | 6.7 | 85.1 | 5.3 | 0.2 | 2.4 |
| 2 | 8.5 | 82.9 | 6.3 | 0.3 | 1.6 |
| 3 | 8.7 | 82.3 | 6.5 | 0.3 | 0.6 |

The results in Table I show that the product mixture changed with time, and the final mixture was lower in trisulfide and higher in disulfide when $CO_2$ was not used, as compared with the results shown in Examples I–II. These results also show that t-butyltrisulfide made without $CO_2$ treatment was susceptible to decomposition during distillation even at lower temperature.

EXAMPLE IV

This is also a comparative example.

The run was carried out the same was as that described in Example III except that after heating at 70° C. for 1 hour, $CO_2$ was not added before vacuum distillation. The vacuum distillation was carried out at 70° C. and 100 torr and GC analyses were performed each hour. The results are shown in Table II.

TABLE II

| Hours of Vacuum distillation | Weight % by GC | | | | |
|---|---|---|---|---|---|
| | Disulfide | Trisulfide | Tetra-sulfide | Penta-sulfide | Mercaptan |
| 0 | 1.4 | 66.1 | 5.9 | 0.1 | 26.0 |
| 1 | 5.0 | 84.0 | 5.7 | 0.1 | 4.6 |
| 2 | 7.3 | 82.6 | 6.7 | 0.1 | 2.9 |
| 3 | 9.5 | 78.7 | 8.9 | 0.2 | 1.5 |

Similar to the results shown in Table I, when $CO_2$ was not used, the trisulfide weight % decreased with increased time and was much lower than that obtained from the invention runs shown in Examples I and II.

EXAMPLE V

This example shows the production of di-t-dodecyl trisulfide.

The following were weighed into a 2 liter, 3-necked flask: 0.35 g of 50% NaOH, 5.32 g of TERGITOL® 15-S-7 (Union Carbide), and 665.5 g (3.29 mole) of t-dodecyl mercaptan. The flask was equipped with a thermowell, magnetic stirring bar, and condenser with $N_2$ inlet on top. Under a $N_2$ atmosphere, the mixture was heated to 75° C. Then 89.9 g (2.84 mole) of elemental sulfur was added in portions over 15 minutes at 75° C. with stirring. Hydrogen sulfide was evolved and was vented to the low pressure flare line after the sulfur addition was complete, the mixture was heated to 130° C. and maintained at this temperature with stirring for 1 hour. Then the mixture was sparged with $N_2$ (about 2 SCFH) for 4 hours at 130° C. with stirring. During the sparging time the condenser was removed. The mixture was cooled to 72° C. and sparging was stopped. At this point the mercaptan sulfur level was 5900 ppm.

A flask equipped with a Dewar condenser containing dry ice with a $N_2$ inlet on top of the condenser was used to treat the crude product produced above. It should be noted that if the procedure was carried out in an autoclave, the Dewar condenser would not be needed since the propylene oxide would be confined in the autoclave. The other condenser used at the beginning of the procedure would also not be needed.

To the crude product at 72° C. was added 3.3 g of NaOH in methanol solution which was made from 2.2 g of methanol and 1.1 g of 50% aqueous NaOH. Then propylene oxide (35.7 g, 43.0 ml) was added over 15 minutes at 72° C. The mixture was heated with stirring for an additional 2.25 hours at 72° C. After this time, the dry ice condenser and addition funnel were replaced by a gas dispersion tube and gas outlet tube connected to a flare line. Carbon dioxide was sparged into the reaction mixture at a rate of 1–2 SCFH for 15 minutes as the mixture cooled to 60° C. Then both $CO_2$ and $N_2$ were bubbled in at the same rate (1–2 SCFH) for the next 45 minutes at 60° C. Sparging with $CO_2$ was stopped with $N_2$ sparging continued for 1 hour additional at 60° C. Total reaction mixture was then filtered (Whatman 1 filter paper) giving a very clear, light yellow di-t-dodecyl trisulfide product (706 g, 100% yield).

The product was stable as shown by an accelerated aging test at 140° F. When the product was put in a bottle with a polyseal cap and was heated for 7 days at 140° F., the mercaptan sulfur value was essentially the same before and after showing no decomposition had occurred.

It should be noted that filtration of the $CO_2$ treated trisulfide gave a much clearer liquid than the one only involving $N_2$ sparging.

In a second invention run, 1.75 g of water was added just before sparging with $CO_2$ as described above. Based on the product obtained and its stability on aging, no advantage could be found for adding the additional water. Results were essentially the same as for the first invention run above.

EXAMPLE VI

This example is a comparative example showing the production of di-t-dodecyl mercaptan without $CO_2$ treatment.

The same procedure as in Example V was used except no $CO_2$ was used. After the propylene oxide treatment at 72° C., sparging was only done with $N_2$ for 2 hours at 60° C. The product was not as stable as when $CO_2$ was used. Accelerated aging tests at 140° F. for 7 days showed that the mercaptan sulfur value increased 3–4 times during aging indicating decomposition was occurring.

It should be noted that filtration of the $CO_2$-treated trisulfide gave a much clearer liquid than the one only involving $N_2$ sparging.

The results shown in the above examples clearly demonstrate that the present invention is well adapted to carry out the objects and attain the ends and advantages mentioned was well as those inherent therein. While modifications may be made by those skilled in the art, such modifications are encompassed within the spirit of the present invention as defined by the disclosure and the claims.

That which is claimed is:

1. A process for producing stablized organic polysulfide comprising (1) contacting a mercaptan with sulfur in the presence of a catalyst comprising a base to produce a product medium comprising a polysulfide; and (2) contacting said product medium with carbon dioxide.

2. A process according to claim 1 wherein said base is selected from the group consisting of triethylamine, trimethylamine, tetramethylammonium hydroxide, tetraethylammonium hydroxide, tetrapropylammonium hydroxide, tetramethylammonium bisulfide, tetraethylammonium bisulfide, lithium hydroxide, sodium hydroxide, potassium hydroxide, calcium hydroxide, magnesium hydroxide, sodium bicarbonate, sodium carbonate, sodium oxide, magnesium oxide, calcium oxide, calcium carbonate, potassium carbonate, sodium phenoxide, barium phenoxide, calcium phenoxide, NaSH, $Na_2S$, $R^1ONa$, $R^1SNa$, and combinations of two or more thereof wherein $R^1$ is a $C_1$–$C_{18}$ alkyl radical.

3. A process according to claim 1 wherein said base is sodium hydroxide.

4. A process according to claim 1 wherein said catalyst further comprises a surfactant selected from the group consisting of alkoxylated compounds, quaternary ammonium salts, alkali metal alkyl sulfates, alkali metal salts of alkanoic acids, alkali metal salts of alkaryl sulfonic acids, 1-alkyl pyridinium salts, and combinations of two or more thereof.

5. A process according to claim 4 wherein said surfactant is selected from the group consisting of alkoxylated mercaptans, alkoxylated alcohols, and combinations of any two or more thereof.

6. A process according to claim 4 wherein said surfactant is an alkoxylated alcohol.

7. A process according to claim 6 wherein said alkoxylated alcohol has a general formula of $R^2O[CH_2CH(R^3)O]_q$ wherein $R^2$ is a hydrocarbyl radical selected from the group consisting of alkyl radical, alkylaryl radical, aryl radical, cycloalkyl radical, alkenyl radical and combinations of two or more thereof; $R^3$ is selected from the group consisting of hydrogen, $C_1$–$C_{16}$ alkyl radical, $C_2$–$C_{16}$ alkenyl radical and combinations of two or more thereof; and q is a number of from 1 to about 20.

8. A process according to claim 6 wherein said alkoxylated alcohol the formula of $R^2O(CH_2CH_2O)_7H$, wherein $R^2$ is a secondary alkyl radical having 11 to 15 carbon atoms.

9. A process according to claim 8 wherein said base is sodium hydroxide.

10. A process according to claim 1 wherein said base is triethylamine.

11. A process according to claim 4 wherein said surfactant is a quaternary ammonium salt.

12. A process according to claim 4 wherein said surfactant is methyltrialkyl($C_8$–$C_{10}$)ammonium chloride.

13. A process according to claim 1 wherein said organic polysulfide is di-t-butyl polysulfide.

14. A process according to claim 1 wherein said organic polysulfide is di-t-dodecyl polysulfide.

15. A process according to claim 9 wherein said organic polysulfide is di-t-butyl trisulfide.

16. A process according to claim 9 wherein said organic polysulfide is di-t-dodecyl trisulfide.

17. A process for producing stabilized organic polysulfide comprising (1) contacting a mercaptan with elemental sulfur in the presence of a catalyst to produce a product medium; and (2) contacting said product medium with dioxide, wherein said polysulfide has about 3 or more sulfur atoms per molecule and said catalyst comprises a base and a surfactant;

said base is selected from the group consisting of tetramethylammonium hydroxide, trimethylamine, triethylamine, tetraethylammonium hydroxide, tetrapropylammonium hydroxide, tetramethylammonium bisulfide, tetraethylammonium bisulfide, lithium hydroxide, sodium hydroxide, potassium hydroxide, calcium hydroxide, magnesium hydroxide, sodium bicarbonate, sodium carbonate, sodium oxide, magnesium oxide, calcium oxide, calcium carbonate, potassium carbonate, sodium phenoxide, barium phenoxide, calcium phenoxide, NaSH, $Na_2S$, $R^1ONa$, $R^1SNa$, and combinations of two or more thereof wherein $R^1$ is a $C_1$–$C_{18}$ alkyl radical; and said surfactant is selected from the group consisting of alkoxylated compounds, quaternary ammonium salts, alkali metal alkyl sulfates, alkali metal salts of alkanoic acids, alkali metal salts of alkaryl sulfonic acids, 1-alkyl pyridinium salts, and combinations of two or more thereof.

18. A process according to claim 17 wherein said surfactant is an alkoxylated alcohol; and said base is sodium hydroxide.

19. A process according to claim 18 wherein said alkoxylated alcohol the formula of $R^2O(CH_2CH_2O)_7H$, wherein $R^2$ is a secondary alkyl radical having 11 to 15 carbon atoms.

20. A process for producing stabilized di-t-butyl polysulfide comprising: (1) contacting t-butyl mercaptan with sulfur in the presence of a catalyst at a temperature in the range of from 50° C. to 150° C. for 30 minutes to 5 hours to produce a product medium; to form a product mixture; wherein said catalyst is prepared by heating sodium hydroxide and an ethoxylated alcohol having the formula of $R^2O(CH_2CH_2O)_7H$ wherein $R^2$ is a secondary alkyl radical having 11–15 carbon atoms; and (2) contacting said product mixture with carbon dioxide.

* * * * *